US007662100B2

(12) United States Patent
Murashita

(10) Patent No.: US 7,662,100 B2
(45) Date of Patent: Feb. 16, 2010

(54) ULTRASONIC DIAGNOSTIC DEVICE

(75) Inventor: Marasu Murashita, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 349 days.

(21) Appl. No.: 10/714,260

(22) Filed: Nov. 14, 2003

(65) Prior Publication Data

US 2004/0122320 A1 Jun. 24, 2004

(30) Foreign Application Priority Data

Dec. 20, 2002 (JP) ............................. 2002-370173

(51) Int. Cl.
*A61B 8/00* (2006.01)
(52) U.S. Cl. ...................... 600/443; 128/916
(58) Field of Classification Search ......... 600/440–441, 600/443, 447, 454–456
See application file for complete search history.

(56) References Cited

U.S. PATENT DOCUMENTS

| | | | |
|---|---|---|---|
| 5,533,510 A | 7/1996 | Koch, III et al. | |
| 5,568,811 A | 10/1996 | Olstad | |
| 5,701,897 A * | 12/1997 | Sano | 600/453 |
| 5,706,816 A | 1/1998 | Mochizuki et al. | |
| 6,217,520 B1 | 4/2001 | He et al. | |
| 6,241,675 B1 * | 6/2001 | Smith et al. | 600/443 |
| 6,245,017 B1 * | 6/2001 | Hashimoto et al. | 600/447 |
| 6,443,894 B1 | 9/2002 | Sumanaweera et al. | |
| 6,527,717 B1 * | 3/2003 | Jackson et al. | 600/437 |
| 7,043,062 B2 * | 5/2006 | Gerard et al. | 382/128 |

FOREIGN PATENT DOCUMENTS

| | | |
|---|---|---|
| JP | 6-285065 | 10/1994 |
| JP | 8-19540 | 1/1996 |
| JP | 3045642 | 3/2000 |
| JP | 2002-306483 | 10/2002 |

(Continued)

OTHER PUBLICATIONS

Olivier Gerard et al., "Efficient model-based quantification of left ventricular function in 3-D echocardiography", *IEEE Transactions on Medical Imaging*, IEEE Inc., New York, US, vol. 21, No. 9, Sep. 2002, pp. 1059-1068.

(Continued)

*Primary Examiner*—Francis J. Jaworski
(74) *Attorney, Agent, or Firm*—William L. Androlia; H. Henry Koda

(57) ABSTRACT

An edge detector executes a process to extract a surface of an inner wall of a left ventricle from a binarized image output from a binarization circuit. A telediastolic edge memory stores an intracardial surface image at the end of ventricular diastole from among intracardial surface images for time phases output from the edge detector. A displacement detector unit detects the amount of displacement for each site of the intracardial surface between time phases from the intracardial surface image at the telediastolic which is output from the telediastolic edge memory, a current intracardial surface image which is output from the edge detector, and a center-of-mass coordinate of the intracardial section at the telediastolic point which is stored in a telediastolic center-of-mass memory. A coloring processor unit applies a coloring process to each site of the surface of the current intracardial surface image based on the amount of displacement and outputs the result to an image synthesizer unit.

13 Claims, 8 Drawing Sheets

FOREIGN PATENT DOCUMENTS

| | | |
|---|---|---|
| JP | 8-66397 | 3/1996 |
| JP | 8-299341 | 11/1996 |
| JP | 9-180001 | 7/1997 |
| JP | 10-33538 | 2/1998 |

OTHER PUBLICATIONS

Johannes Behr et al., "Modelling, visualization, and interaction techniques for diagnosis and treatment planning in cardiology", *Computers & Graphics*, Pergamon Press Ltd., Oxford, GB, vol. 24, No. 5, Oct. 2000, pp. 741-753.

Chinese Office Action of Apr. 20, 2007.

"Significance of stress echocardiography for ischemic heart disease", written by Naoko Yasugi and Samon Koyanagi, Supplemental Issue of *Clinical Laboratory Test*, published by Igaku-Shoin Ltd., Oct. 30, 2001, vol. 45, No. 11, pp. 1315-1320.

* cited by examiner

ULTRASONIC DIAGNOSTIC DEVICE

BACKGROUND OF THE INVENTION

1. Field of the Invention

The present invention relates to an ultrasonic diagnostic device and in particular to a three-dimensional ultrasonic diagnostic device for measuring and diagnosing movement of a target tissue.

2. Description of the Related Art

Ultrasonic diagnosis devices are used for diagnosing abnormal movement of a target tissue, for example, abnormal expansion and retraction movements of a heart. In order to diagnose abnormal movement of a target tissue, it is desirable to use an ultrasonic diagnostic device which can precisely capture the movement of the target tissue. To achieve this object, in conventional ultrasonic diagnostic devices, a two-dimensional ultrasonic image in which the outline of the target tissue is clarified is obtained for each frame, a displacement image corresponding to a difference between an image of an earlier frame and an image of the most recent frame is time sequentially synthesized to form a displacement history image, and the displacement history image is displayed (refer to, for example, Japanese Patent No. 3045642). With a two-dimensional ultrasonic diagnostic device having such functionality, it is possible to detect abnormal movements of target issue and positions where an abnormality occurred in the target tissue with a high degree of sensitivity.

With the development of ultrasonic technologies, it has become possible to employ for diagnosis three-dimensional ultrasonic diagnostic devices which can three-dimensionally express a target tissue within a three-dimensional space. The advantages of such three-dimensional ultrasonic diagnostic devices are particularly significant in the ultrasonic observation and diagnosis of an organ such as the heart. For example, by observing the expansion and retraction movements of the heart using a three-dimensional diagnostic device, it is possible for a user to comprehend the three-dimensional shape of the heart, which is much more difficult with two-dimensional ultrasonic diagnostic devices. The advantages of the comprehension of the three-dimensional shape are also true in a displacement history image in the conventional ultrasonic diagnostic device as described above. That is, by realizing a display method in a three-dimensional ultrasonic diagnostic device which allows visual comprehension of the displacement of the target tissue, it is possible to more precisely diagnose abnormal movements of a heart.

SUMMARY OF THE INVENTION

The present invention advantageously provides a three-dimensional ultrasonic diagnostic device which can be used to precisely diagnose abnormal movements of a target tissue.

According to one aspect of the present invention, there is provided an ultrasonic diagnostic device comprising an echo data obtaining unit for transmitting and receiving an ultrasonic wave to and from a three-dimensional space including a target tissue and obtaining three-dimensional echo data for each time phase; a displacement information creator unit for creating displacement information by calculating an amount of displacement for each site on the surface of the target tissue based on the three-dimensional echo data for each of the time phases; a displacement-present image formation unit for forming, based on the three-dimensional echo data and the displacement information, a three-dimensional displacement-present image in which displacement of each site on the surface of the target tissue is shown on a tissue image three-dimensionally representing the target tissue; a two-dimensional display image formation unit for projecting the three-dimensional displacement-present image onto a plane to form a two-dimensional display image; and a display for displaying the two-dimensional image.

With this structure, because a three-dimensional displacement-present image represents an amount of displacement on a tissue surface, for example, by forming the three-dimensional displacement-present image with the inner wall of the left chamber of the heart as the tissue surface, the position of an infarction can be very easily identified.

According to another aspect of the present invention, it is preferable that the ultrasonic diagnostic device further comprises a straight line setting unit for setting a plurality of straight lines extending along a radial direction from the reference point which is the center of mass of the target tissue, and that the displacement information creator unit calculates a position of an intersection between each of the straight lines and the surface of the target tissue based on the three-dimensional echo data for each of the time phases and calculates the amount of displacement based on a change in the position of the intersection for the same straight line between time phases.

When displacements on straight lines extending along a radial direction from the center of mass are observed, the structure can be preferably used for diagnosis of abnormal movements of an organ which expands from and retracts to the center such as, for example, a heart.

According to another aspect of the present invention, it is preferable that, in the ultrasonic diagnostic device, a coloring process using colors determined for the amount of displacement of each site is applied.

With this structure, the coloring process allows for identification of a region where the amount of displacement is very small, which is preferable for diagnosis of, for example, a site of a myocardial infarction.

According to yet another aspect of the present invention, there is provided an ultrasonic diagnostic device comprising a reference point identifier unit for identifying a reference point corresponding to the structure of the target tissue and a movement calculator unit for calculating an amount of movement of the target tissue between time phases based on the identified reference point.

With such a structure, because the amount of displacement of each site can be determined with the amount of overall movement of the target tissue corrected, or, more preferably, completely cancelled out, the structure is very effective for observing movements of the target tissue itself without the overall movement of the target tissue associated with, for example, a deviation of a probe for transmitting and receiving the ultrasonic waves or the overall movement of the target tissue caused by movements of other tissues.

DESCRIPTION OF PREFERRED EMBODIMENT

Figure 1:
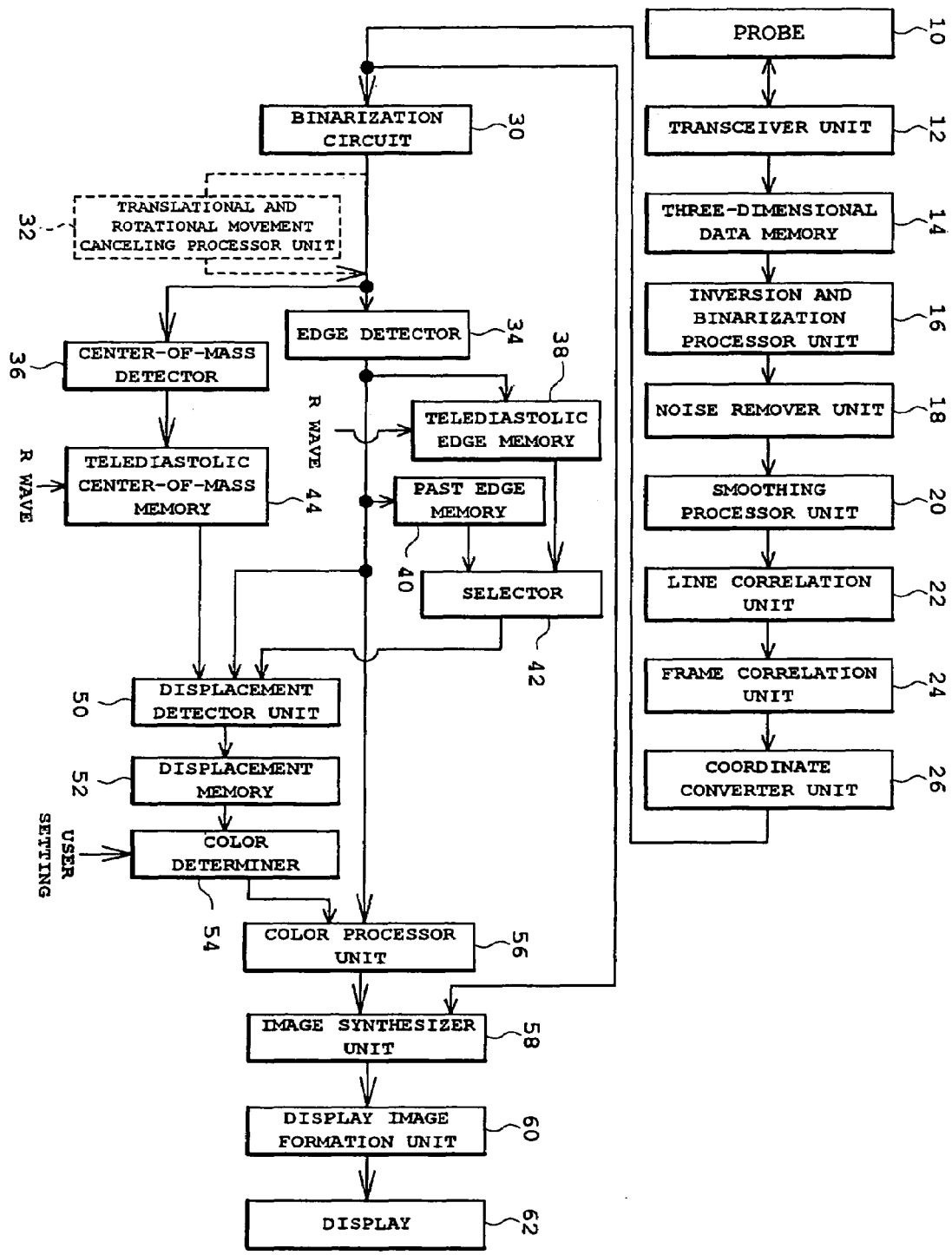
FIG. 1 is a block diagram showing an ultrasonic diagnostic device according to a preferred embodiment of the present invention.

A preferred embodiment of the present invention will now be described while referring to the drawings.

FIG. 1 is a block diagram showing an overall structure of an ultrasonic diagnostic device according to a preferred embodiment of the present invention. A transceiver unit 12 transmits and receives an ultrasonic wave via a probe 10 into and from a space including a left ventricle of a heart which is a target tissue. Echo data within a three-dimensional space including the left ventricle of the heart is obtained for each volume in each time phase and stored in a three-dimensional data memory 14. An inversion and binarization processor 16 applies an inversion process and a binarization process to an echo value in the echo data in each voxel stored in the three-dimensional data memory 14. More specifically, voxels corresponding to an intracardial section within the left ventricle having relatively small echo values are set as voxels having a high brightness value and voxels corresponding to other sections having relatively large echo values are set as voxels having a low brightness value. A noise remover unit 18, a smoothing processor unit 20, a line correlation unit 22, and a frame correlation unit 24, apply image processes, primarily for the purpose removing a high frequency noise component, is applied to the high and low brightness value voxels to which inversion and binarization processes are applied.

The noise remover unit 18 determines a voxel as a noise when the voxel is spatially isolated and has a different brightness value from surrounding voxels, and converts the brightness value of the noise voxel. For example, when the brightness value of a target voxel differs from the brightness value of all 26 surrounding voxels spatially adjacent to the target voxel, the brightness value of the isolated target voxel having a different brightness value is converted to the same brightness as that of the surrounding voxels. The smoothing processor unit 20 calculates an average value of brightness values among a target voxel and 26 surrounding voxels adjacent to the target voxel for each brightness value of voxel output from the noise remover unit 18 and newly sets the calculated result as the brightness value of the target voxel. The line correlation unit 22 applies an averaging process between lines to the brightness value of each voxel output from the smoothing processor unit 20 in a two-dimensional frame forming a volume at a particular time phase. The frame correlation unit 24 applies an averaging process to the brightness value of each voxel between two-dimensional frames forming a volume at a particular time phase. The brightness values of voxels converted into various brightness values in the smoothing processor unit 20, line correlation unit 22, and frame correlation unit 24 are output to a coordinate converter unit 26. The coordinate converter unit 26 converts the coordinate values of the voxels from an R, θ, φ coordinate system with the probe as the reference to an X, Y, Z coordinate system with a cube as the reference.

A binarization circuit 30 includes a comparator and etc., applies a binarization process based on a predetermined threshold value to an ultrasonic image output from the coordinate converter unit 26 made of voxels having various brightness values, to form a binarized image made of two types of voxels, one corresponding to the intracardial section of the left ventricle and the other corresponding to the other regions, and outputs the binarized image to an edge detector 34 and a center-of-mass detector unit 36. The output of the binarization circuit 30 may instead be input to the edge detector 34 and the center-of-mass detector unit 36 through a translational and rotational movement canceling processor unit 32. The details of the translation and rotational movement canceling processor unit 32 will be described below with reference to FIG. 8.

The edge detector 34 performs an extraction process for extracting the surface of the inner wall of the left ventricle from the binarized image output from the binarization circuit 30. The edge detector 34 will now be described with reference to FIG. 2.

Figure 2:
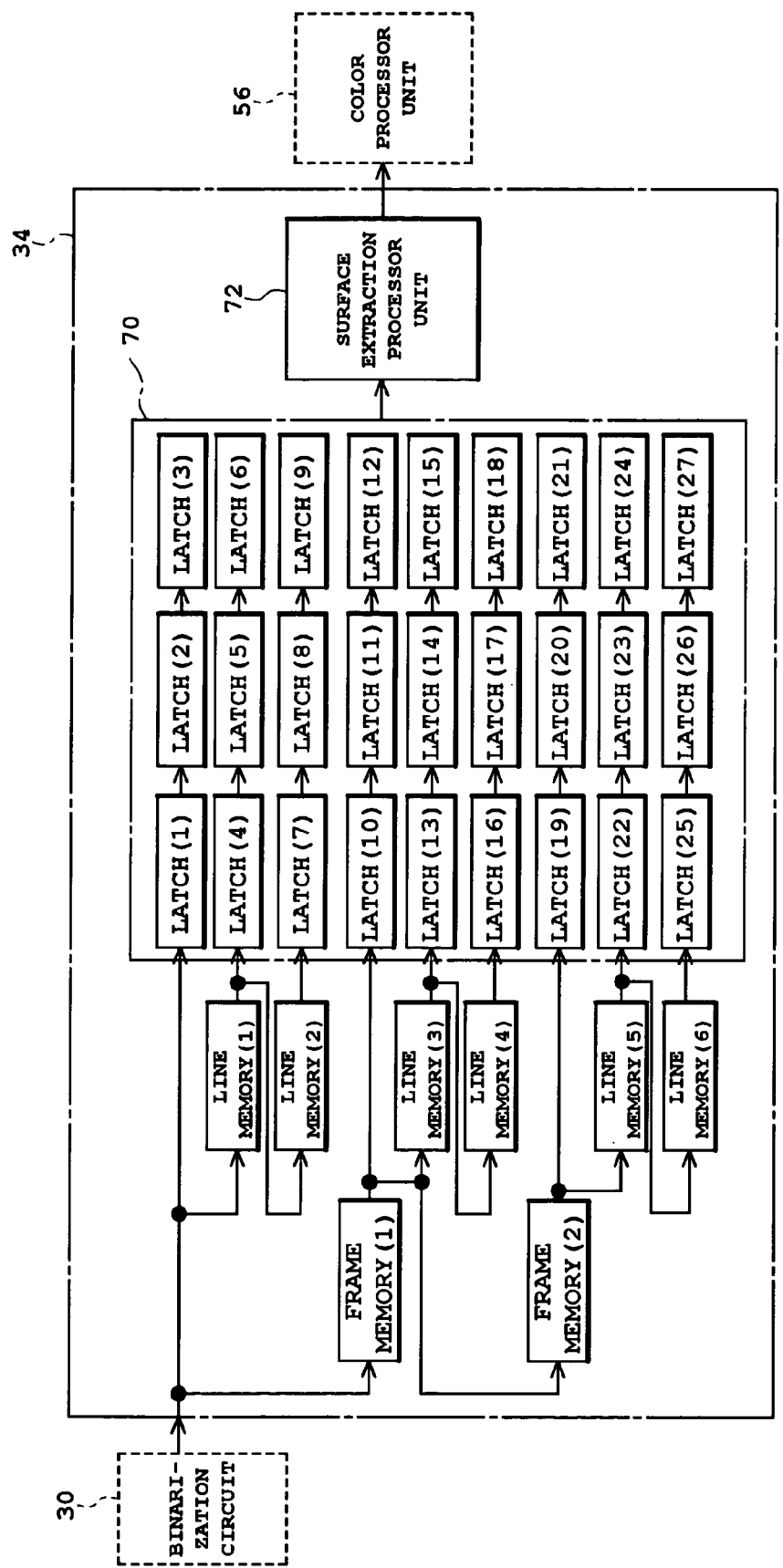
FIG. 2 is a block diagram showing an internal structure of an edge detector.

FIG. 2 is a block diagram showing an internal structure of an edge detector. The edge detector 34 has two frame memories (1) and (2), six line memories (1) through (6), a voxel data memory 70, and a surface extraction processor unit 72. The output from the binarization circuit 30 is output as a voxel data array in the order of abutting on the image in units of echo values (voxel data) for voxels forming a volume in each time phase. In other words, in a voxel data array forming a particular volume, voxel data is arranged, in order, from a first frame to the last frame forming the volume, and, in each frame, the voxel data is arranged in order from a first line to the last line forming the frame.

The frame memory is a memory for storing the voxel data array in units of frames and for outputting the stored data. Thus, the frame memory functions as a delay buffer for one frame. The line memory is a memory for storing the voxel data array in units of lines and for outputting the stored data. Thus, the line memory functions as a delay buffer for one line. That is, the output of the frame memory (1) is voxel data for the frame just before the voxel data output from the binarization circuit 30 and the output of the frame memory (2) is voxel data for the frame which is two frames before the voxel data output from the binarization circuit 30. In this manner, current voxel data, voxel data which for the previous frame, and voxel data for the frame before the previous frame are all input into the voxel data memory 70.

Similarly, the output of the line memory (1) is voxel data one line before the voxel data output from the binarization circuit 30, the output of the line memory (2) is voxel data two lines before the voxel data output from the binarization circuit 30, the output of the line memory (3) is voxel data one line before the voxel data output from the frame memory (1), the output of the line memory (4) is voxel data two lines before the voxel data output from the frame memory (1), the output of the line memory (5) is voxel data one line before the voxel data output from the frame memory (2), and the output of the line memory (6) is voxel data two lines before the voxel data output from the frame memory (2). In this manner, to the voxel data memory 70, voxel data of a total of 9 lines are input, 3 lines which abut within the current frame, 3 corresponding lines within the previous frame, and 3 corresponding lines within a frame which is two frames prior.

The voxel data memory 70 has a total of 27 latches, three for each of the 9 lines. The three latches corresponding to each line are for extracting data for 3 sequential voxels on a line.

In this manner, the voxel data output from the latch (14) is set as a target voxel and a group of 27 voxel data in which 26 voxel data adjacent to the target voxel are added is output to the surface extraction processor unit 72.

The surface extraction processor unit 72 determines the target voxel as a surface voxel of an intracardial section when the data of the target voxel is voxel data corresponding to the intracardial section and at least one of 26 adjacent surrounding voxel data is voxel data corresponding to the other sites. By finding surface voxels with every voxel within a volume of each time phase as a target voxel, a group of voxels forming the surface of the intracardial section in each volume, that is, an intracardial surface image (outline image of the inner wall of ventricle) is obtained. The intracardial surface image formed for each volume is output to a telediastolic edge memory (reference numeral 38 in FIG. 1) or the like.

Referring again to FIG. 1, the telediastolic edge memory 38 stores the intracardial surface image at the telediastolic point of the ventricle, selected from among the intracardial surface images of each time phase output from the edge detector 34. An R wave of the cardiographic waveforms is input to the telediastolic edge memory 38 and the telediastolic moment is determined based on the R wave generated at ventricular diastole. A past edge memory 40 is a memory for temporarily storing an intracardial surface image at each time phase output from the edge detector 34 for each time phase. A selector 42 selects one of an intracardial surface image at the telediastolic point output from the telediastolic edge memory 38 and an intracardial surface image at a past time phase output from the past edge memory 40, and outputs the selected image to a displacement detector unit 50. The selection operation by the selector 42 is performed based on instructions from a user.

A binarized image output from the binarization circuit 30 is also input to the center-of-mass detector unit 36, which then calculates the coordinates of the center of mass of the intracardial section based on the input image. In some cases, the image of the intracardial section may not have a shape wherein the outer surface is completely closed. In such a case, the calculation of the center of mass may be performed with the target being a region of interest which is set in advance to surround the intracardial section. A telediastolic center-of-mass memory 44 stores the coordinates of the center of mass of the intracardial section at the point of telediastolic of the ventricle. The R wave of the cardiographic waveform is input to the telediastolic center-of-mass memory 44, and the telediastolic center-of-mass memory 44 determines the telediastolic point based on the R wave generated at the end of ventricular diastole.

A displacement detector unit 50 is provided for detecting an amount of displacement between time phases for each section within the intracardial surface. One of the intracardial surface images output from the telediastolic edge memory 38 and an intracardial surface image of a past time phase output from the past edge memory 40 are input to the displacement detector unit 50 via the selector 42. A current intracardial surface image output from the edge detector 34 is also input to the displacement detector unit 50, and the coordinates of the center of mass of the intracardial section at the telediastolic point which is stored in the telediastolic center-of-mass memory 44 is input to the displacement detector unit 50. The displacement detector unit 50 detects the amount of displacement based on this input information. A detection method of the amount of displacement by the displacement detector unit 50 will now be described referring to FIG. 3.

Figure 3:
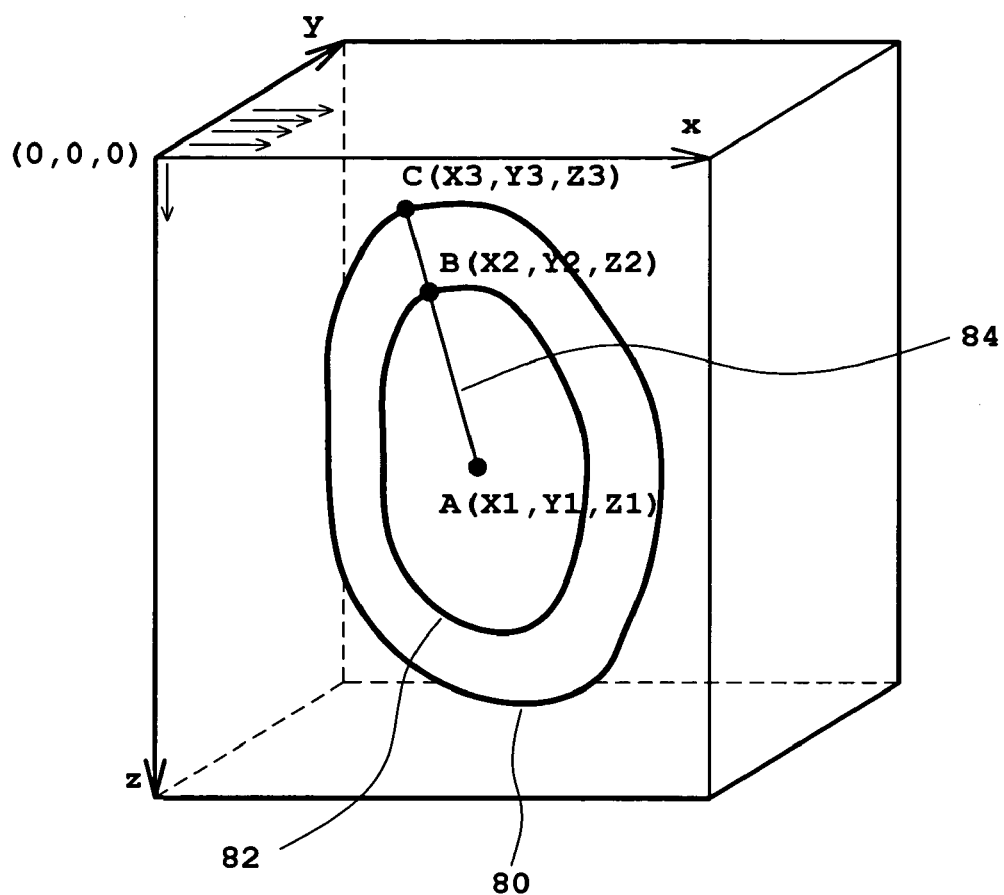
FIG. 3 is an explanatory diagram for a detection method of an amount of displacement.

FIG. 3 is an explanatory diagram of method of detecting an amount of displacement performed by a displacement detector unit (reference numeral 50 in FIG. 1) and shows an intracardial surface image 80 at the point of telediastolic and a current intracardial surface image 82. A coordinate A (X1, Y1, Z1) represents the coordinates of the center of mass of the intracardial section at the point of telediastolic.

First, the displacement detector unit identifies surface sections within the current intracardial surface image for which an amount of displacement is to be measured. Various methods can be employed to identify the surface sections. For example, it is possible to sequentially move a point of interest from an origin (0, 0, 0) in the X direction, Y direction, and Z direction to detect surface sections and set all detected surface sections as a target. Alternatively, it is also possible to set sample points from the detected surface sections. It is still further possible for the user to identify surface sections while viewing the ultrasonic wave imaged is played on a display. A surface section determined through any method is set as a coordinate B (X2, Y2, Z2).

The coordinates C (X3, Y3, Z3) of an intersection of a straight line 84 passing through point A (a point at coordinate A) and point B (a point at coordinate B) and an intracardial surface image 80 at the telediastolic point are calculated. By then finding then distance between point B and point C (the point at coordinate C) determined in this manner, the displacement of the surface section (point B) from the telediastolic is determined. In some cases, the outer surface of the image of the intracardial section may not be a completely closed shape, and the coordinate C of the intersection between the straight line 84 and the intracardial surface image 80 at the point of telediastolic therefore cannot be calculated. In such a case, it is determined that the amount of displacement cannot be calculated, and other points A and B are set to continue calculation of the amount of displacement. When the output of the past edge memory (reference numeral 40 in FIG. 1) is selected by the selector (reference numeral 42 in FIG. 1), the above-described detection method of displacement can be applied in a similar manner by replacing the surface image indicated by the reference numeral 80 in FIG. 3 by the intracardial surface image of a past time phase.

Referring again to FIG. 1, the amounts of displacement in each section within the surface of the intracardial section detected by the displacement detector unit 50 are stored in a displacement memory 52. A color determiner 54 determines colors for each site within the surface of the intracardial section based on the amount of displacement. In other words, the color determiner 54 reads the amount of displacement of a target surface site from the displacement memory 52 and sets the color absolutely determined in advance for each amount of displacement as the color of this target site. A color determination method by the color determiner 54 will now be described referring to FIG. 4.

Figure 4:
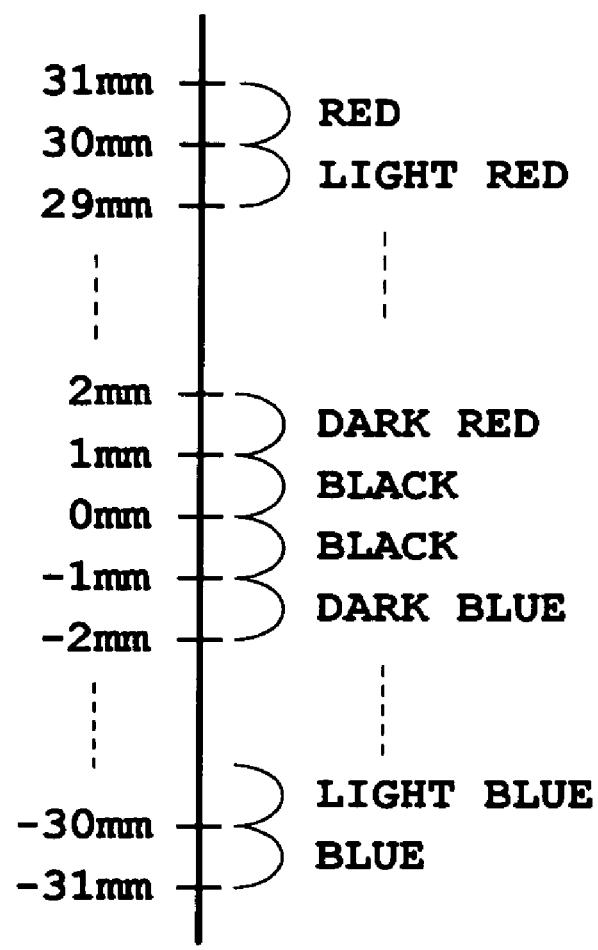
FIG. 4 is a diagram showing example colors determined for various amounts of displacement.

FIG. 4 is a diagram showing example colors absolutely determined for each amount of displacement. As shown in FIG. 4, when the displacement of a site is within a range of 30 mm to 31 mm, a color "red" is assigned and when the displacement is within a range of 29 mm to 30 mm, a color "light red" is assigned. When the displacement is a negative displacement, a "blue" color is assigned. The amount of displacement becomes negative when the displacement is in the expansion direction while the ventricle is retracting or when the displacement is in the retraction direction while the ventricle is expanding. The correspondence relationship between the amounts of displacement and the colors may also be determined based on an external setting by a user. For example, it is possible to set the amount of displacement corresponding to "red" to be within a range from 40 mm to 41 mm or to set the amount of displacement corresponding to "yellow" to be within a range from 30 mm to 31 mm. The color determined in this manner for each section of the surface of the intracardial section is output to a coloring processor unit (reference numeral 56 in FIG. 1).

Referring again to FIG. 1, the coloring processor unit 56 applies a coloring process to the current intracardial surface image output from the edge detector 34 based on the color of teach section of the surface determined by the color determiner 54 and outputs the result to an image synthesizer 58. The image synthesizer 58 synthesizes a three-dimensional image output from the coordinate converter unit 26 which includes the intracardial section and the colored intracardial surface image output from the coloring processor unit 56 to form a three-dimensional image. A display image formation unit 60 forms a two-dimensional display image in which the three-dimensional image is projected onto a plane. When the display image formation unit 60 projects the three-dimensional image onto a plane, a rendering calculation may be performed based on a volume rendering method to form a two-dimensional display image in which the inside of the target tissue is transparently displayed. For example, the method disclosed in Japanese Patent Laid-Open Publication No. Hei 10-33538 may be preferably employed as the rendering calculation based on the volume rendering method. The method described in this reference can be briefly summarized as follows. First, a plurality of rays (which match, for example, the ultrasonic beam) are set in a three-dimensional space. For each ray, echo values are referenced in order and a rendering calculation is performed for each echo value in sequence. In parallel to this operation, multiplication with each opacity (degree of non-transparency) is performed. When the multiplied value becomes 1 or greater, the rendering calculation for the ray is completed and the rendering calculation result at this point is determined as the two-dimensional display pixel value corresponding to the ray. By determining a pixel value for each ray, a two-dimensional display image in which the inside of the target tissue is transparently displayed can be formed as a collection of the pixel values.

The two-dimensional display image formed by the display image former unit 60 is displayed on a display 62.

Figure 5A:
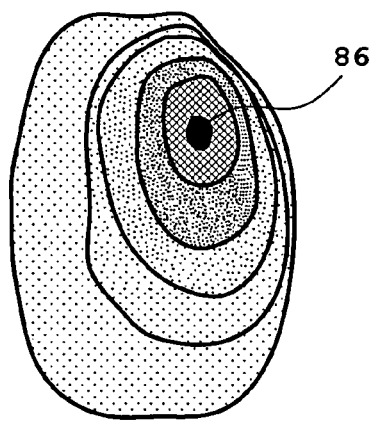
FIG. 5 is a diagram showing a display image including a displacement-present image obtained using the ultrasonic diagnostic device of FIG. 1.
Figure 5B:
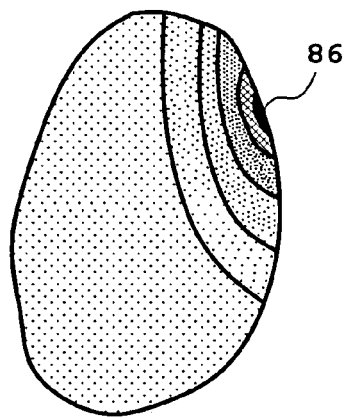

FIG. 5 is a diagram showing a display image including a displacement-present image obtained by the ultrasonic diagnostic device of FIG. 1 and shows the intracardial section of the left ventricle of a heart. Images (A) and (B) are display images of the same three-dimensional image seen from different viewpoints, and one or both images (A) and (B) are shown on the display. FIG. 5 shows images to which the coloring process has been applied using colors based on the amount of displacement of each section of the surface of the intracardial section (refer to FIG. 4). The section 86 is displayed in "black" to indicate a displacement within a range of −1 mm to 1 mm. Thus, it can be seen that the section 86 is moving very slowly and can be deduced as a diseased section affected by an infarction or the like.

Figure 6:
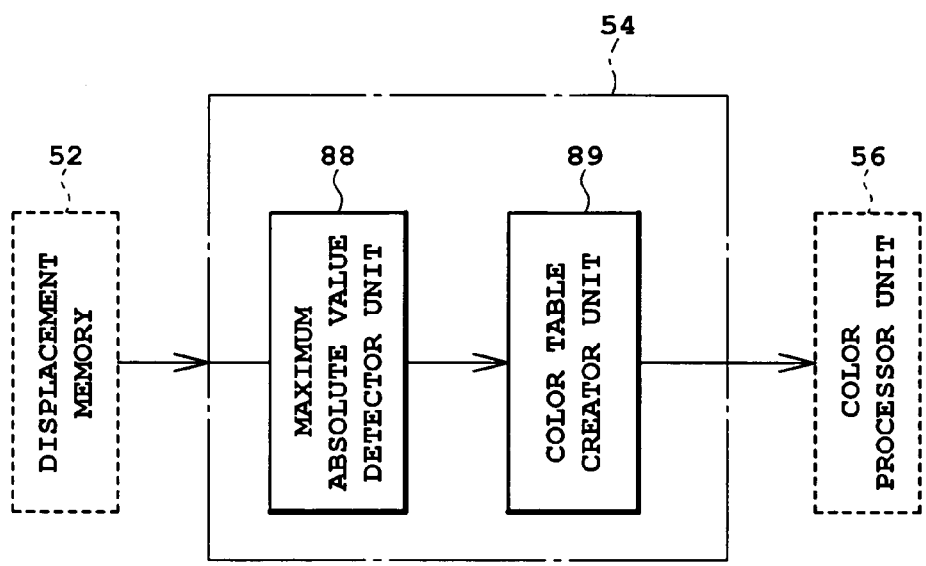
FIG. 6 is a diagram showing another form of color determiner.

FIG. 6 shows another form of the color determiner 54 of FIG. 1. The color determiner 54 shown in FIG. 6 determines color, for each site within the surface of the intracardial section, based on a relative magnitude of displacement of each site with respect to displacements of a plurality of sites. The color determiner 54 of FIG. 6 includes a maximum absolute value detector unit 88 and a color table creator unit 89. The maximum absolute value detector unit 88 detects a displacement having a maximum absolute value from among the amounts of displacement stored in the displacement memory (reference numeral 52 of FIG. 1). For example, when the displacement is distributed between −5 mm to 18 mm, an absolute value of "18 (mm)" is detected as the maximum absolute value from comparison between "18 (mm)" and "5 (mm)".

The color table creator unit 89 sets a relative displacement region based on the maximum absolute value detected by the maximum absolute value detector unit 88 and sets "(maximum absolute value) X (−1)" as a minimum value and the "maximum absolute value" as a maximum value. That is, when the maximum absolute value is "18 (mm)", the relative displacement region becomes −18 mm to +18 mm. Then, the color table creator unit 89 generates a color table in which displayable color gradations are distributed between the maximum and minimum values of the relative displacement region. FIG. 7 shows an example of a color table created by the color table creator unit 89.

Figure 7A:
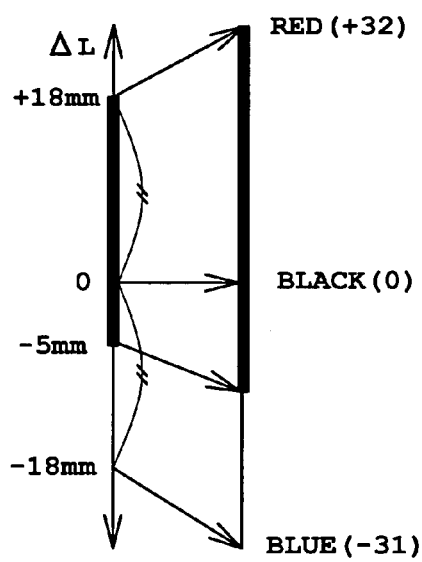
FIG. 7 is a diagram showing an example of a color table created by a color table creator unit.
Figure 7B:
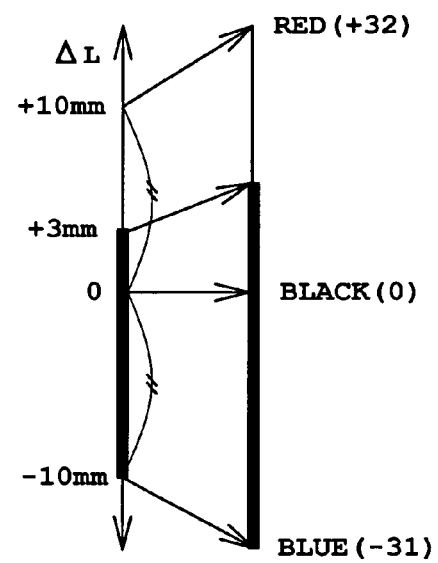

In the example shown in FIG. 7(A), the displacement AL is distributed between −5 mm and +18 mm, and the maximum and minimum displayable color gradations are respectively "red (+32)" and "blue (−31)". In this case, the range of gradations from +32 to −31 is assigned to a range of displacements of +18 mm to −18 mm. In the example shown in FIG. 7(B), the displacement AL is distributed between −10 mm and +3 mm, and the maximum and minimum displayable color gradations are "red (+32)" and "blue (−31)". In this case, the range of gradations from +32 to −31 is assigned to a range of displacements from +10 mm to −10 mm. By determining color for each site based on the displacements of all sites in this manner, it is possible to maximize the efficiency of use of the displayable color gradations. The generated color table is output to the coloring processor unit (reference numeral 56 of FIG. 1). In the coloring processor unit, a coloring process is applied based on the color table to color the current intracardial surface image output from the edge detector (reference numeral 34 of FIG. 1) using a color corresponding to the displacement of each site.

Figure 8:
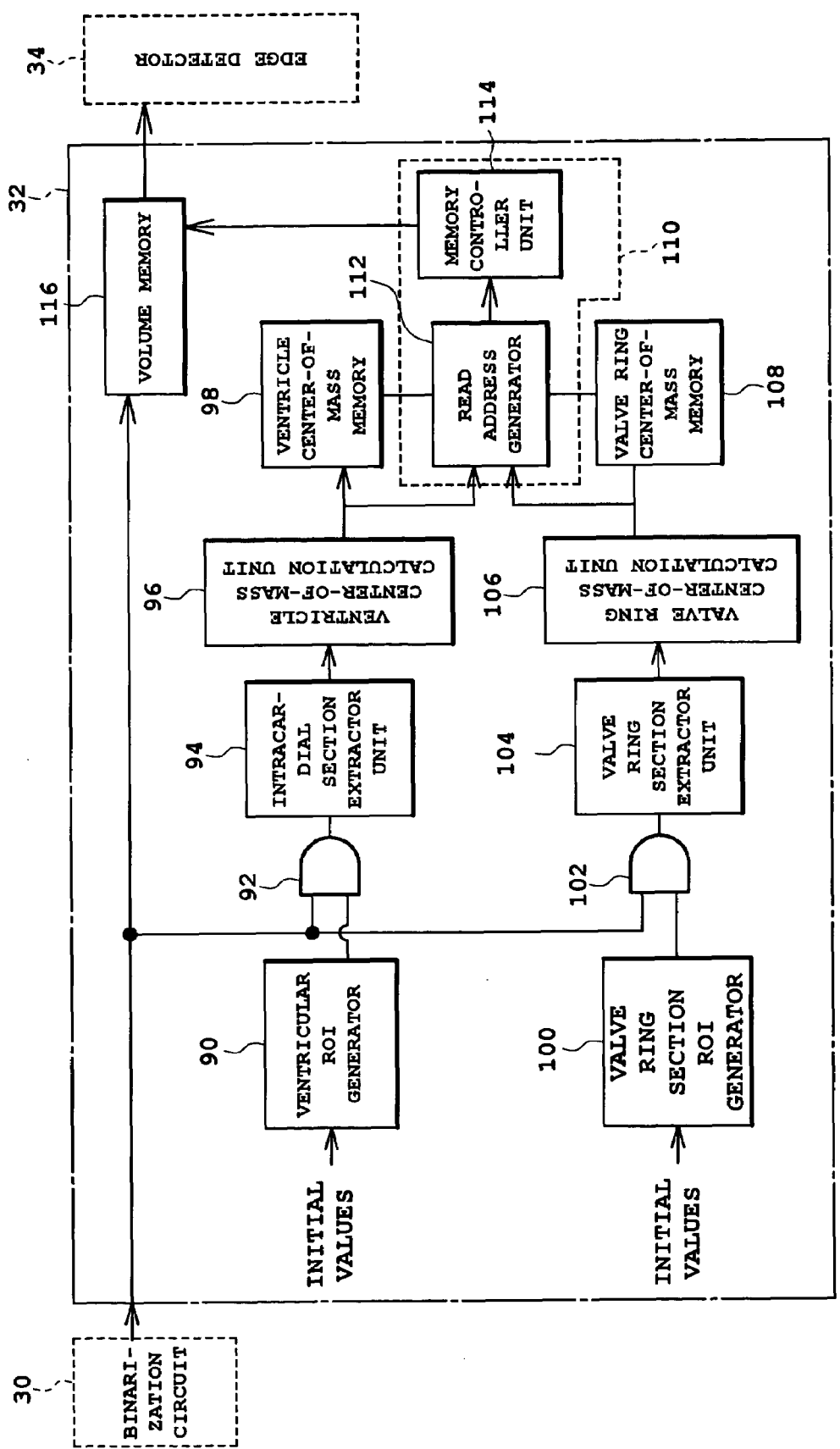
FIG. 8 is a block diagram showing an internal structure of a translational and rotational movement canceling processor.

FIG. 8 is a block diagram showing an internal structure of a translational and rotational movement canceling processor unit shown in FIG. 1. A ventricular ROI (region of interest) generator 90 generates coordinates of an ROI forming the periphery of the ventricle of a heart, which is a target tissue. The ROI for a ventricle may, for example, have an elliptical shape, and the user will set the initial values such as the lengths of the major and minor axes, position of the center, and slope of the ellipse while viewing the ultrasonic image so that the image of the ventricle fits within the ROI. In this process, the user determines, using a trackball or the like, the initial values while viewing the ultrasonic wave image and observing movement of one heartbeat so that the ROI includes the left ventricle of the heart in all frames. The setting of the ROI is not limited to manual setting by a user, but may also be automatically set based on the movement of the ventricle.

A ventricular gate circuit 92 is a circuit which allows only the echo data within the ROI for the ventricle to pass through. In other words, coordinates of an ROI output from the ventricular ROI generator 90 is input to one of the input terminals of the ventricular gate circuit 92 so that only the echo data of coordinates within the ventricle ROI are extracted from a binarized image input to the other input terminal. The extracted data is output to an intracardial extractor unit 94. The intracardial extractor unit 94 extracts an intracardial image within the ventricle from the binarized image in the ROI. A ventricle center-of-mass calculator unit 96 calculates, for each frame, the coordinates of a center of mass in an image of the inside of the ventricle output from the intracardial extractor unit 94. The calculated coordinates of the center of mass of the ventricle are output to a read address generator 112 and a ventricle center-of-mass memory 98.

A valve ring ROI (region of interest) generator 100 generates coordinates of an ROI forming a periphery of a valve ring section positioned on the end of a ventricle. The ROI for valve ring has, for example, an elliptical shape, and the user sets the initial values such as the lengths of the major and minor axes of the ellipse, position of the center, and slope of the ellipse while viewing the ultrasonic wave image so that the valve ring section fits into the ROI. In this process, the user determines, using a trackball or the like, the initial values while viewing the ultrasonic wave image and observing movement for one heart beat so that the ROI includes the valve ring section in all frames. The setting of the ROI is not limited to a manual setting by the user and may also be mechanically set based on the movement of the valve ring.

A valve ring gate circuit 102 is a circuit which allows only the echo data within the valve ring ROI to pass through. That is, coordinates of the ROI output from the valve ring ROI generator 100 are input to one of the input terminals of the valve ring gate circuit 102, so that just the echo data of the coordinates within the valve ring ROI are extracted from a binarized image input to the other input terminal. The extracted echo data is output to a valve ring section extractor unit 104. The valve ring section extractor unit 104 extracts an image of the valve ring section from the binarized image within the ROI. A valve ring center-of-mass calculator unit 106 calculates coordinates of the center of mass of the valve ring section for each frame of a valve ring image output from the valve ring extractor unit 104. The calculated coordinates of the center of mass of the valve ring section are output to the read address generator 112 and a valve ring center-of-mass memory 108.

The ventricle center-of-mass memory 98 stores coordinates of the center of mass of ventricle at the point of telediastolic. As a trigger used to inform the telediastolic, an R wave of the cardiographic waveform is used. In other words, using the R wave obtained at the point of telediastolic as a trigger, the coordinates of the center of mass of the ventricle output from the ventricle center-of-mass calculator unit 96 are stored as the coordinates of the center of mass of ventricle at its telediastolic point. Similarly, the coordinates of the center of mass of the valve ring at the telediastolic is stored from the valve ring center-of-mass calculator unit 106 to the valve ring center-of-mass memory 108 using the R wave as the trigger.

A read controller unit 110 comprises a read address generator 112 and a memory controller unit 114, and reads echo data from the binarization circuit (reference numeral 30 in FIG. 1) so as to form an ultrasonic wave image in which the translational and rotational movements of the ventricle between volumes are cancelled. More specifically, the read address generator 112 obtains the coordinates of the center of mass of the ventricle at the point of telediastolic from the ventricle center-of-mass memory 98 and coordinates of the center of mass of the valve ring section at the point of telediastolic from the valve ring center-of-mass memory 108. The read address generator 112 further obtains the coordinates of the center of mass of the ventricle in the current volume from the ventricle center-of-mass calculator unit 96 and the coordinates of the center of mass of the valve ring section in the current volume from the valve ring center-of-mass calculator unit 106.

The read address generator 112 calculates a read address so that the center of mass of the ventricle of the current volume overlaps the center of mass of the ventricle at the telediastolic, and, at the same time, a straight line passing through the center of mass of the ventricle and the center of mass of the valve ring in the current volume overlaps a straight line passing through the center of mass of the ventricle and the center of mass of the valve ring at the telediastolic point.

In the volume memory 116, a copy of the echo data output from the binarization circuit 30 is stored for each volume, along with the address of the original image. The memory controller unit 114 reads the echo data from the volume memory 116 according to the read address calculated by the read address generator 112 and outputs the read data to the edge detector (reference numeral 34 in FIG. 1) and the center-of-mass detector unit (reference numeral 36 in FIG. 1). As a result, the echo data output from the volume memory 116 is output in the form of an image in which the translational and rotational movements have been cancelled.

A preferred embodiment of the present invention has been described. It should be understood, however, that the above-described embodiment is for exemplifying purpose only and is not in any way intended to limit or restrict the scope of the present invention.

What is claimed is:

1. An ultrasonic diagnostic device comprising:
   an echo data obtaining unit for transmitting and receiving an ultrasonic wave to and from a three-dimensional space including a target tissue and obtaining three-dimensional echo data for each time phase;
   a displacement information creator unit for creating displacement information by calculating an amount of displacement for each site on the surface of the target tissue based on the three-dimensional echo data for each of the time phases;
   a displacement-present image formation unit for forming, based on the three-dimensional echo data and the displacement information, a three-dimensional displacement-present image in which displacement of each site on the surface of the target tissue is shown on a tissue image three-dimensionally representing the target tissue;
   a two-dimensional display image formation unit for projecting the three-dimensional displacement-present image onto a plane to form a two-dimensional display image;
   a display for displaying the two-dimensional image; and
   a reference identifier unit for identifying, based on the three-dimensional echo data for each of the time phases, a reference point based on the structure of the target tissue, wherein
   the displacement information creator unit calculates said amount of displacement for each site by calculating a distance between each site on the surface of the target tissue and the reference point based on the three-dimensional echo data for each of the time phases and a change in the distance between time phases of each site on the surface of the target tissue.

2. An ultrasonic diagnostic device according to claim 1, further comprising:
   a straight line setting unit for setting a plurality of straight lines extending along a radial direction from the reference point which is the center of mass of the target tissue, wherein
   the displacement information creator unit calculates a position of an intersection between each of the straight lines and the surface of the target tissue based on the three-dimensional echo data for each of the time phases and calculates the amount of displacement based on a change in the position of the intersection for the same straight line between time phases.

3. An ultrasonic diagnostic device according to claim 2, wherein the displacement-present image creator unit applies a coloring process to each of the sites on the tissue image based on the amount of displacement of that site to form the three-dimensional displacement-present image.

4. An ultrasonic diagnostic device according to claim 3, wherein the coloring process is a coloring process using colors absolutely determined for the amount of displacement of each site.

5. An ultrasonic diagnostic device according to claim 3, wherein the coloring process is a coloring process using a color determined based on a relative magnitude of the amount of displacement in each site with respect to the amounts of displacement of the plurality of sites.

6. An ultrasonic diagnostic device according to claim 3, wherein the two-dimensional display image is formed by projecting the three-dimensional displacement-present image onto a plane using a volume rendering method.

7. An ultrasonic diagnostic device comprising:
an echo data obtaining unit for transmitting and receiving an ultrasonic wave to and from a three-dimensional space including a target tissue and obtaining three-dimensional echo data for each time phase;
a reference point identifier unit for identifying, based on the three-dimensional echo data for each of the time phases, a reference point based on the structure of the target tissue;
a movement calculator unit for calculating an amount of movement of the target tissue between the time phases based on the identified reference point;
a displacement information creator unit for creating displacement information by correcting the amount of movement based an the three-dimensional echo data for each of the time phases and calculating an amount of displacement for each site on the surface of the target tissue, wherein the displacement information creator unit calculates said amount of displacement for each site by calculating a distance between each site on the surface of the target tissue and the reference point based on the three-dimensional echo data for each of the time phases and a change in the distance between time phases of each site on the surface of the target tissue;
a displacement-present image formation unit for forming a three-dimensional displacement-present image in which the amount of displacement of each site on the target tissue surface is represented on a tissue image which three-dimensionally represents the target tissue, based on the three-dimensional echo data and the displacement information;
a two-dimensional display image formation unit for forming a two-dimensional display image by projecting the three-dimensional displacement-present image onto a plane; and
a display for displaying the two-dimensional display image.

8. An ultrasonic diagnostic device which:
transmits and receives an ultrasonic wave to and from a three-dimensional space including a target tissue to obtain three-dimensional echo data for each time phase;
creates displacement information by calculating an amount of displacement for each site on the surface of the target tissue based on the three-dimensional echo data for each time phase;
forms a three-dimensional displacement-present image in which an amount of displacement of each site on the target tissue surface is represented over a tissue image which three-dimensionally represents the target tissue, based on the three-dimensional echo data and the displacement information;
forms a two-dimensional display image by projecting the three-dimensional displacement-present image onto a plane and displays the formed two-dimensional display image; and
identifies, based on the three-dimensional echo data for each of the time phases, a reference point based on the structure of the target tissue, wherein
the ultrasonic diagnostic device calculates a distance between each site on the surface of the target tissue and the reference point based on the three-dimensional echo data for each of the time phases and calculates the amount of displacement based on a change in the distance between the time phases.

9. An ultrasonic diagnostic device according to claim 8, which further:
sets a plurality of straight lines extending along a radial direction from the reference point which is a center of mass of the target tissue, wherein
the ultrasonic diagnostic device calculates a position of an intersection between each of the straight lines and the surface of the target tissue based on the three-dimensional echo data for each of the time phases and calculates the amount of displacement based on a change in the position of the intersection for the same straight line between the time phases.

10. An ultrasonic diagnostic device according to claim 8 wherein a coloring process is applied to each of the sites on the tissue image based on the amount of displacement of that site, to form the three-dimensional displacement-present image.

11. An ultrasonic diagnostic device according to claim 10, wherein the coloring process is a coloring process using a color absolutely determined for the amount of displacement of each site.

12. An ultrasonic diagnostic device according to claim 10, wherein the coloring process is a coloring process using a color determined based on a relative magnitude of the amount of displacement in each site with respect to the amounts of displacement of the plurality of sites.

13. An ultrasonic diagnostic device according to claim 8, wherein the two-dimensional display image is formed by projecting the three-dimensional displacement-present image onto a plane using a volume rendering method.

* * * * *